(12) United States Patent
Muggetti et al.

(10) Patent No.: US 7,201,913 B1
(45) Date of Patent: Apr. 10, 2007

(54) ORAL FORMULATIONS FOR ANTI-TUMOR COMPOUNDS

(75) Inventors: Lorena Muggetti, Meda (IT); Alessandro Martini, Milan (IT); Paola Civaroli, Milan (IT); Christopher James, Arese (IT)

(73) Assignee: Pfizer Inc., New York, NY (US)

( * ) Notice: Subject to any disclaimer, the term of this patent is extended or adjusted under 35 U.S.C. 154(b) by 233 days.

(21) Appl. No.: 10/110,225

(22) PCT Filed: Oct. 2, 2000

(86) PCT No.: PCT/EP00/09647

§ 371 (c)(1),
(2), (4) Date: Aug. 15, 2002

(87) PCT Pub. No.: WO01/30351

PCT Pub. Date: May 3, 2001

(30) Foreign Application Priority Data

Oct. 22, 1999  (GB) .................................. 9925127.4

(51) Int. Cl.
*A61K 9/20* (2006.01)
*A61K 9/48* (2006.01)
*A61K 9/14* (2006.01)
*A61K 31/44* (2006.01)

(52) U.S. Cl. ...................... 424/400; 424/451; 424/464; 424/489; 514/280

(58) Field of Classification Search ................ 424/400, 424/450, 435

See application file for complete search history.

(56) References Cited

U.S. PATENT DOCUMENTS

| 5,433,951 A | | 7/1995 | Serajuddin et al. | ......... 424/486 |
| 5,552,156 A | | 9/1996 | Burke | ........................ 424/450 |
| 5,741,524 A | * | 4/1998 | Staniforth et al. | .......... 424/489 |
| 5,908,835 A | * | 6/1999 | Bissery | ......................... 514/33 |
| 5,954,998 A | * | 9/1999 | Zhou et al. | ............. 252/186.25 |
| 6,201,014 B1 | * | 3/2001 | Gardiner | ..................... 514/463 |
| 6,248,771 B1 | * | 6/2001 | Shenoy et al. | .............. 514/418 |
| 6,531,139 B1 | * | 3/2003 | Gao et al. | .................... 424/400 |
| 6,569,452 B1 | * | 5/2003 | Civaroli et al. | ............. 424/451 |
| 6,573,290 B1 | * | 6/2003 | Love | .......................... 514/406 |

FOREIGN PATENT DOCUMENTS

| WO | 96 11669 | 4/1996 |
| WO | 99 06031 | 2/1999 |
| WO | 99 42086 | 8/1999 |

\* cited by examiner

*Primary Examiner*—Gollamudi S. Kishore
(74) *Attorney, Agent, or Firm*—Steve Zelson; David L. Kershner

(57) ABSTRACT

The present invention relates to a semi-solid filling medium which comprises a camptothecin derivative; a pharmaceutically acceptable carrier matrix which is a polyglycolized glyceride; and an effective thickening-reducing and stabilizing-promoting amount of one or more pharmaceutically acceptable excipients.

19 Claims, No Drawings

ORAL FORMULATIONS FOR ANTI-TUMOR COMPOUNDS

FIELD OF THE INVENTION

The present invention provides an oral dosage form for camptothecin derivatives, such as, for example, irinotecan (7-ethyl-10-[4-(1-piperidino)-1-piperidino]carbonyloxy camptothecin or its pharmaceutically acceptable salts, especially hydrochloride (CPT-11); or topotecan (9-dimethy-laminomethyl-10-hydroxy-camptothecin) or its pharmaceutically acceptable salts, especially hydrochloride.

BACKGROUND OF THE INVENTION

Camptothecins are a new class of cytotoxic agents, which have been undergoing both preclinical and clinical testing against various solid tumors. The nuclear enzyme topoisomerase I (Topo I), along with the other topoisomerases, functions to resolve topological problems during DNA replication. These enzymes are the target for camptothecin and its derivatives. These agents are derivatives of an extract from the Chinese tree Camptotheca acuminata, and were originally shown to be active against L1210 murine leukemia (Wall, M. E., Wani, M. C., CoY, C. E., Palmer, K. H., MCPhail, A. T. and Sim, G. A.: Plant antitumor agents. 1. The isolation and structure of camptothecin, a novel alkaloidal leukemia and tumor inhibitor from Camptotheca acuminata, J. Chem. Soc., 88:3888, 1966). Further study confirmed that alkaline labile DNA (single strand) breaks were formed when camptothecin was added to cells in tissue culture and that the breaks rapidly resealed after removal of the drug. These DNA single strand breaks represent the nicks that form when camptothecin stabilizes the covalent adducts between genomic DNA and the reparative nuclear enzyme topo I (Horwitz, S. B., Change. C. S. C. K. and Grollman, A. P.: Studies on camptohtecin. 1. Effects on nucleic acid and protein synthesis. Mol. Pharmacol, 7:632, 1971; Hsiang, Y. H. and Liu, L. F: Identification of mammalian DNA topoisomerase I as an intracellular target of the anticancer drug Camptothecin. Cancer Res., 48: 1722, 1988). Early studies also showed maximal S-phase toxicity, and that the topo I-associated DNA single strand nicks led to the formation of more persistent double strand breaks which ultimately resulted in cell death. Camptothecins also appear to have other cytotoxic effects which amount for their activity in human tumor xenografts that typically have low S-phase fractions, though these effects are to be clearly defined.

A number of more soluble and less toxic analog of camptothecin have been developed, among them CPT-11 and topotecan hydrochloride are commercial products.

Topotecan hydrochloride is indicated for the treatment of metastatic carcinoma of the ovary after failure of initial or subsequent chemotherapy and for the treatment of small cell lung cancer sensitive disease after failure of first-line chemotherapy.

CPT-11 has been studied extensively in both preclinical and clinical trails and has shown good anti-tumor activity against a broad spectrum of experimental tumor models (Kunimoto, T., Nitta, K., Tanaka, T. Uchara, N., Baga, H., Takeuchi, M., Yokokura, T., Sawada, S., Miyasaka, T. and Mutai, M.: Antitumor activity of 7-ethyl-10-[4-(1-piperidino)-1-piperidino]carbonyloxycamptothecin, against murine tumors. Cancer Res., 47:5944, 1987). It has recently received FDA approval for the treatment of colon cancer. Developed in 1983, CPT-11 is a semi-synthetic derivative of camptothecin which is, in effect, a prodrug converted to 7-ethyl-10-hydroxy-camptothecin (SN-38), following hydrolysis in the liver.

The intravenous drug form of CPT-11 is being developed for the treatment of colorectal cancer.

It is well known that parenteral administration of antitumor drugs such as, for example, camptothecin derivatives, is associated with some intrinsic disadvantages and drawbacks, e.g., patient discomfort or the requirement for the patient to travel to the physician's office for drug administration, with obvious results in patient inconvenience.

Thus the need has arisen to develop oral formulations of anti-tumor drugs that would allow to overcome the inconvenience and the discomfort of the patient that are associated with the parenteral way of administration.

Classical oral formulations are, for example, solid oral dosage forms, that are medication delivery systems presented as solid dose units readily administered by mouth. The group includes tablets, capsules, cachets and pills, as well as bulk or unit-dose powders and granules. The group constitutes the most popular form of presentation, and tablets and capsules account for the greatest number of preparations in this category.

It has long been known in the pharmaceutical industries that capsules are a convenient form for the oral administration of a variety of active agents because of their relative ease of manufacture (compared with other dosage forms such as tablets), flexibility of size and dose. Capsules have traditionally been used for powder or granule formulations but, in recent years, capsules have been adapted to contain the active ingredient in the form of paste, semi-solid or liquid formulation.

Since, for example, CPT-11 and topotecan hydrochloride are classified as class I cytotoxic agents, any form of leakage from the dosage form would present a safety concern.

The risk of leakage of a cytotoxic agent from a formulation as a tablet or powder-filled capsule, both during manufacturing and distribution, is extremely high.

Thus, in light of the above mentioned problem about the safe handling of these drugs, it is desirable to formulate them in a filling medium which is semi-solid and can be readily introduced and maintained into capsules without the expected problem of leakage.

In particular, a thermoplastic hot-melt type capsule formulation can be suitable for enhancing stability and for minimizing leakage concerns.

A problem to be solved when manufacturing a capsule filled with a semi-solid matrix, especially when it comprises a high concentration of an active such as a camptothecin derivative in the formulation, is the thickening, i.e. the increase of semi-solid matrix viscosity over time. The thickening of the semi-solid mass has repercussions not only on the manufacturing of the formulation (e.g. non-homogeneity of the formulation and impossibility to partition the formulation into capsules), but also on the reproducibility of the release profile of the active ingredient from the formulation itself.

A further problem to be faced regards the chemical and physical stability of the semi-solid filling matrix with aging. Several examples are described in the scientific literature, where semi-solid matrix systems change their physical state and their pharmaceutical characteristics with time and storage in different humidity/temperature conditions. As examples, SanVicente et al. clearly shows that the dissolution rate from glyceride matrices decreases with time (Proceedings of the $2^{nd}$ World Meeting APGI/APV, Paris May 25–28, 1998, p. 261–2); and Sutananta W. et al. clearly shows the effect of aging on the physical properties of similar matrices, explored by DSC and tensile strength measurements (International Journal of Pharmaceutics, 111 (1994) 51–62).

Both the above mentioned problems were experienced when formulation activities for manufacturing a semi-solid matrix formulation for a camptothecin derivative were performed, especially when a semi-solid matrix comprises high concentrations of said camptothecin derivative.

There is therefore a need to find a formulation approach which allows to overcome thickening problems and to secure the maintenance of the physico-chemical characteristics of the semi-solid filling medium during manufacturing and storage.

It has now been surprisingly found that, by adding an effective amount of one or more excipients chosen from: a lecithin, a phospholipid, a pharmaceutical acceptable oil, a polyethylenglycol, and a saturated or unsaturated mono-, di- or triglyceride to the carrier matrix in which the camptothecin derivative is dispersed or dissolved, the above-mentioned problems can be solved.

DESCRIPTION OF THE INVENTION

Accordingly, the present invention provides a pharmaceutical composition suitable for oral administration which comprises a camptothecin derivative, a pharmaceutically acceptable carrier matrix which is a polyglycolized glyceride, and at least one pharmaceutically acceptable excipient chosen from a lecithin, a phospholipid, a pharmaceutically acceptable oil, a polyethyleneglycol, and a saturated or unsatured mono-, di- or triglyceride.

The said pharmaceutically acceptable excipient is typically contained in the composition of the invention in an amount effective to reduce thickening and promote stabilisation of the combination of the camptothecin derivative and the carrier matrix.

The pharmaceutical composition of the invention has a semi-solid consistency and can therefore conveniently be used as a filling inside a capsule for oral administration. The composition is accordingly hereafter also referred to as a semi-solid filling medium.

Preferably, the excipient used in the composition of the invention is a lecithin selected from different types of commercially available lecithins.

The use of a compound chosen from a lecithin, a phospholipid, a pharmaceutically acceptable oil, a polyethyleneglycol and a saturated or unsaturated mono-, di- or triglyceride as an excipient in the composition of the invention has the effect of reducing thickening and promoting stability of the carrier matrix in which the camptothecin derivative is dispersed or dissolved.

The present invention provides a first process for producing a pharmaceutical composition of the invention as defined above, which process comprises adding an effective amount of the or each said pharmaceutically acceptable excipient to a solution or dispersion of a camptothecin derivative in the polyglycolised glyceride. In addition the invention provides a second process for producing a pharmaceutical composition of the invention as defined above, which process comprises dissolving or dispersing a camptothecin derivative in a molten homogenous mixture of the polyglycolyzed glyceride and the or each said pharmaceutically acceptable excipient. In both process embodiments the resulting composition is stabilised and has controlled viscosity owing to the presence of the excipients.

The present invention also provides an oral formulation which comprises a capsule shell and, as a filling, a pharmaceutical composition as defined above. This oral formulation may take the form of a capsule. In one aspect of the invention the oral formulation is for use in the treatment of a human cancer.

The present invention is particularly advantageous for the production of oral solid dosage forms which can be prepared by filling capsules with the pharmaceutical composition (semi-solid medium) of the invention, using standard techniques. A capsule consisting of a capsule shell and capsule filling, wherein the filling comprises a pharmaceutical composition of the invention as described above, is also an object of the present invention.

Examples of the camptothecin derivative which is used in the present invention include irinotecan and its pharmaceutically acceptable salts, in particular the hydrochloride (CPT-11), topotecan and its pharmaceutically accceptable salts, in particular hydrochloride, SN-22, SN-38, 9-amino-20(S)-CPT. 9-nitro-20(S)-CPT (rubitecan); preferably it is CPT-11 or topotecan hydrochloride; more preferably it is CPT-11.

Camptothecin derivatives described in the U.S. Pat. No. 5,843,954, in the name of Kabushik Kaisha Yakult Honsha and Daiichi Pharm. Co. Ltd, may also be used in the present invention.

According to the present invention, the amount of camptothecin derivative per unit dose is in the range of from about 1 mg to about 100 mg, preferably from about 5 mg to about 100 mg.

The carrier matrix used in the composition of the invention is a polyglycolyzed glyceride. Polyglycolyzed glycerides which can be used in the present invention are generally mixtures of known monoesters, diesters and triesters of glycerols and known monoesters and diesters of polyethylene glycols with a mean relative molecular mass between about 200 and 6000. They may be obtained by partial transesterification of triglycerides with polyethylene glycol or by esterification of glycerol and polyethylene glycol with fatty acids using known reactions. Preferably, the fatty acid contains 8–22 carbon atoms, particularly 8–18 carbon atoms. Examples of natural vegetable oils, which may be used, include palm kernel oil and palm oil. However, these are only example. The polyol suitably has a molecular weight in the range of about 200–6000 and preferably contains polyethylene glycols, although other polyols may be employed, such as, for instance, polyglycerole and sorbitol. They are known under the trademark Gelucire® and are commercially available from Gattefossé s.a., Saint Priest, France.

Further, two or more polyglycolyzed glycerides may be mixed in order to adjust both the Hydrophilic-Lipophilic Balance (HLB) value and the melting point to a desired value. The HLB value and melting point of the composition may further be adjusted with the addition of components such as polyethylene glycols, polyethylene glycol fatty acid esters and fatty acid alcohols. According to the present invention, it is well within the skill of the artisan to mix the polyglycolysed glycerides to obtain desired HBL values and melting points.

HLB (Hydrophilic-Lipophilic Balance) scale is a numerical scale, extending from 0 to 14, where lower numbers denote more lipophilic and hydrophobic substances and higher numbers denote more hydrophilic and liphophobic substances. The wide range of available polyglycolyzed glycerides allows the selection of the proper matrix according to the processing and release requirements of the formulation. For example, it is possible to achieve either prompt or sustained drug release depending on the thermal and HLB nature of the polyglycolyzed glyceride used as the matrix. According to the present invention, the amount of the carrier matrix is in the range of from about 70% to about 99.9% (w/w), preferably from about 80% to about 95% (w/w) of the pharmaceutical composition.

In particular, the saturated polyglycolyzed glyceride known under the trade name Gelucire® 44/14 is used, as a carrier matrix, according to the present invention.

When a camptothecin derivative such as, e.g. CPT-11, is dispersed or dissolved in the molten polyglycolyzed glyceride mass, a thickening phenomenon (increase in viscosity over time) has been experienced. In this case, thickening made capsule filling process very difficult after a few hours from the beginning of the capsule preparation process arising severe concerns on the development of such formulations. This problem is typically encountered and put in evidence when, in particular, high concentrations of the camptothecin derivative such as, e.g., CPT-11 or topotecan hydrochloride, are dispersed or dissolved in a polyglycolyzed glyceride. In fact, particularly when the active drug substance represents a significant amount of the semi-solid mass, this can have a deep influence on the physical behavior of the matrix.

Furthermore, although described as largely chemically inert materials with good long-term stability, it is reported in the literature that polyglycolyzed glycerides may exhibit aging effects. This phenomenon can result in a change of the physical properties of the matrix, largely influencing the reproducibility of the drug release profile during storage. In summary, not only manufacturing problems, but also instability problems are to be faced by a skilled artisan. The present inventors have thus carried out an extensive investigation. As a result, it has been found that one or more suitable excipients, capable of reducing thickening and promoting the stability (i.e. securing the maintenance) of the physico-chemical characteristics of the semi-solid filling medium during manufacturing and storage, can be chosen among the chemical classes of: lecithins; phospholipids; pharmaceutical acceptable oils, e.g. soybean oils and the like, polyethylenglycols and saturated or insaturated mono-, di- or triglicerides. A preferred excipent is a lecithin selected from the different types of lecithins commercially available, in particular the lecithin known under the trade name Epikuron 135F®.

As stated in the Martindale Extra Pharmacopeia, lecithin is 'a phospholipid composed of a complex mixture of acetone-insoluble phosphatidyl esters (phosphatides) which consist chiefly of phosphatidyl choline, phosphatidyl ethanolamine, phosphatidyl serine, and phosphatidyl inositol, combined with various amounts of other substances such as triglycerides, fatty acids, and carbohydrates, as separated from the crude vegetable oil source. The consistency of both natural grades and refined grades of lecithin may vary from plastic to fluid, depending upon the content of free fatty acid and oil, and upon the presence or absence of other diluents'.

In particular, the semi-solid filling medium of the invention may contain, at least one soybean lecithin fraction with an enriched phosphatidylcholine content such as, e.g., Epikuron 135F®, commercially available from LUCAS MEYER GmbH&Co—Hamberg—Germany.

According to the present invention, the amount of the excipient is in the range of about 0.1% to about 30% (w/w), preferably from about 5 to about 15% w/w of the semi-solid filling medium.

In a preferred embodiment, the present invention provides a semi-solid filling medium which comprises CPT-11, Gelucire 44/14 and a soybean lecithin with an enriched phosphatidylcholine content such as, e.g., Epikuron 135F®. The semi-solid filling medium may optionally contain a dispersing, and/or solubilizing agent, and/or a surfactant, and/or viscosity modifiers, and/or an oral absorption promoter.

A dispersing agent includes cellulose and its derivatives, e.g., carboxymethylcellulose and natural gums; a solubilizing/oral absorption promoter agent includes cyclodextrins, ethanol, triacetin, propylen glycol, glycerides, medium and long chain fatty acid, polyoxyethylene hydrogenated or non-hydrogenated vegetable oils derivatives; a surfactant includes poloxamers, medium chain triglycerides, ethoxylated esters, polyglycerol esters, polyoxyethylene alkyl ethers, sorbitan esters, polyoxyethylene sorbitan fatty acid esters; a viscosity modifier includes hydrogenated or non-hydrogenated vegetable oils, glycerol esters, polyglycerol esters and propylene glycol esters.

The semi solid filling medium according to the invention may also optionally contain chemical stabilizing-promoting agents such as antioxidants and chelating agents.

The semi solid filling medium may optionally comprise one or more additional active drug substances, comprising, for example, antitumor antibiotics such as, e.g. anthracyclines; thymidylate synthase inhibitors including, e.g., capecitabine; epidermal growth factor receptor inhibitors; antimicrotubule agents including, e.g., taxanes comprising, e.g. paclitaxel and docetaxel and vinca alkaloids; angiogenesis inhibitors including, e.g. thalidomide, SU 5416 and SU 6668; chemosensitisers; cyclooxygenase-2 (COX-2) inhibitors including, e.g., celecoxib, valdecoxib, parecoxib and rofecoxib; aromatase inhibitors; alkylating agents including, e.g., estramustine phosphate; antimetabolites; hormonal agents including, e.g., tamoxifen; platinum analogues including, e.g., cisplatin, carboplatin and oxaliplatin; octreotide; glutamine and leucovorin.

A semi-solid filling medium according to the invention may be prepared by means of conventional techniques known to one of ordinary skill in the art.

Typically, a semi-solid filling medium is a dispersion or a solution of the active ingredient in a thermosoftening hot melt inert carrier prepared by mixing or homogenization and filled into capsules as liquid using fluid-filling pumps and allowed to solidify at ambient temperature. The major advantage of semi-solid media is the safety during manufacturing, being the drug dispersed/dissolved in a liquid mass. At ambient condition such a formulation is solid, providing better chemical stability and minimizing leakage problems.

As an example, the semi-solid medium to be filled into capsules may be prepared by adding a camptothecin derivative to a molten homogenous mixture of a polyglycolyzed glyceride and a suitable excipient such as, e.g., a lecithin. This is then followed by through mixing of the molten mass and capsule filling using standard techniques.

Gelatin, gelatin-PEG, starch, hydroxypropylmethylcellulose (HPMC) or casein shell capsules can be chosen as oral dosage forms for a semi-solid filling medium according to the invention.

The pharmaceutical composition of the invention can be administered to a mammal including a human that may need the beneficial effects of a camptothecin derivative formulation described in the invention. The capsules according to this invention may therefore be used to treat a variety of different cancer types including, without limitation, human cancers of the colon, breast, lung, prostate, melanoma, pancreas, liver, stomach, brain, kidney, uterus, cervix, ovaries and urinary tract.

Preferably, when the capsule comprises CPT-11, it can be used for treating a colon cancer, in particular colorectal cancer.

Although the examples reported in the description consider the use of CPT-11, this formulation approach may be applicable to any other camptothecin derivative.

The following examples are given with the purpose to better illustrating the invention but in no way they must be considered as a limitation of the scope of the invention itself.

Example 1

Method of Preparation

For each preparation a proper quantity of the selected Gelucire® was melted at 60° C. under magnetic stirring. The required amount of melted Gelucire® (5 mL) was withdrawn by means of a manual pipette (e.g. Brand-Transferpettor or the like) and added to the required quantity of CPT-11 (500 mg). The drug was dispersed in the molten matrix under magnetic stirring at 60° C. for two hours.

The obtained dispersion was then filled into size 0 hard gelatine capsule (0.5 mL/capsule) using a manual pipette.

The capsules manufactured as described above were tested for dissolution rate according to USP Basket method; 100 rpm; 37° C. in simulated gastric fluid pH 1.2 without enzymes Results In the following Table 1 the release profile of CPT-11 from different Gelucire® based systems are shown. The higher is the hydrophilicity of the excipient (the hydrophilicity value is given by the second figure of the identification code that is index of the Hydrophilic-Lipophilic Balance (HLB) value—the higher is the number, the more hydrophilic is the excipient—) the faster is the release profile.

The results are expressed as percent of the active released from the formulation vs. the theoretical as a function of time. The composition of each formulation was basically 50 mg of CPT-11 dispersed in 0.5 ml of the appropriate Gelucire® per capsule.

TABLE 1

| | % CPT-11 RELEASED (percent of the theoretical) | | | |
|---|---|---|---|---|
| TIME (minutes) | Gelucire ® 44/14 | Gelucire ® 50/13 | Gelucire ® 35/10 | Gelucire ® 46/07 |
| 15 | 29.51 | 0.53 | 1.20 | 0.0 |
| 30 | 74.82 | 2.15 | 2.68 | 0.21 |
| 60 | 87.76 | 4.33 | 7.15 | 0.53 |
| 120 | 91.73 | 9.78 | 17.72 | 1.07 |
| 180 | 92.53 | 15.94 | 26.60 | 1.64 |

Example 2

The following example shows the cases where the thickening of the semisolid matrix systems loaded with CPT-11 was experienced and where not.

Method of Preparation

The formulations containing Gelucire® as the sole component were prepared as described in Example 1.

For each preparation containing a mixture of different components, the semi-solid matrix was prepared by mixing the selected materials at 60° C. under magnetic stirring for 15 minutes.

The required amount of melted semi-solid matrix (5 mL) was withdrawn by means of a manual pipette (e.g. Brand-Transferpettor or the like) and added to the required quantity of CPT-11 (500 mg). The drug was carefully dispersed in the molten matrix under magnetic stirring at 60° C.

After 2, 24 and 48 hours, where it was possible, 0.5 ml samples of the molten matrix were withdrawn by means of a manual pipette and filled into hard gelatine capsules.

Results

The manufacturing of capsule after 2, 24 or 48 hours was impossible for some of the formulations tested (Table 2). The impossibility of withdrawing of samples, due to the thickening of the mass, is a clear index of physical transformation of the semi-solid matrix and of difficulties or impossibility to manufacture any dosage form with such compositions. When the same experiment is performed on the excipients per se (without the active), no thickening was experienced. This is the clear demonstration that this effect is due to a physical interaction between the excipients and CPT-11.

TABLE 2

| | | WORKABILITY AT 60° C. (TIME OF THE WITHDRAWAL) | | |
|---|---|---|---|---|
| Batch Number | SEMISOLID MATRIX BASE | 2 HOURS | 24 HOURS | 48 HOURS |
| ND01645 | Gelucire 44/14 | Y | N | — |
| ND01648 | Gelucire 44/14: Gelucire 46/07 1:1 (v/v) | Y | N | — |
| ND01649 | Gelucire 50/13 | Y | N | — |
| ND01653 | Gelucire 35/10 | Y | N | — |
| ND01671 | Gelucire 44/14: Akoline MCM 9:1 (v/v) | Y | Y | Y |
| ND01672 | Gelucire 44/14: Epikuron 135F 9:1 (v/v) | Y | Y | Y |
| ND01673 | Gelucire 44/14: Emultop 9:1 (w/w) | Y | Y | Y |
| ND01681 | Gelucire 44/14: RyloMG18 9:1 (w/w) | Y | Y | Y |
| ND01691 | Gelucire 44/14: Epikuron 135F 95:5 (v/v) | Y | Y | Y |
| ND01692 | Gelucire 44/14: Epikuron 135F 98:2 (v/v) | Y | Y | Y |

Y = withdrawal allowed
N = withdrawal not allowed by the thickening of the mass
Akoline MCM = mono/diglyceride of medium chain fatty acid (primarily caprylic and capric acids)
Emultop = soybean lecithin
RyloMG18 = glyceril monostearate As shown in the above Table 2, Gelucires® cannot be used per se for formulating CPT-11, due to the evident thickening Mixtures of Gelucires® with Akoline MCM, Epikuron 135F, Emultop and RyloMG18 do not present such thickening issue.

Example 3

In the following Table 3 the dissolution rate profiles of CPT-11 from the formulation ND01671 described in Example 2, containing Gelucire® 44/14 and AkolineMCM 9:1 v/v as components of the semi-solid matrix, are shown as a function of the manufacturing time. Samples of 0.5 ml were withdrawn from the molten mass stirred at 60° C., after 2 hours (column 'A') and 48 hours (column 'B') and partitioned in capsules. The dissolution rate tests were performed with the USP Basket method; 100 rpm; 37° C. in Simulated Gastric Fluid pH 1.2 without enzymes. The data are expressed as percent of the active released from the formulation. The theoretical unit dosage strength is 50 mg CPT-11 per capsule.

The results obtained clearly show that the longer is the molten mass stirring time at 60° C. before partitioning into capsules, the lower is the release profile when the capsule formulation are tested for dissolution rate.

This effect, highlighted during a control in process of the manufacturing process, can be considered predictive of what is going to happen to formulations with aging.

TABLE 3

| Time | Percent of CPT-11 released from the formulation | |
|---|---|---|
| (minutes) | 'A' | 'B' |
| 15 | 59.40 | 0.86 |
| 30 | 84.97 | 2.33 |
| 60 | 86.72 | 13.95 |
| 120 | 86.54 | 43.85 |
| 180 | 87.27 | 70.27 |
| 240 | 87.77 | 84.13 |

Example 4

In the following Table 4 the dissolution rate profiles of CPT-11 from the formulation ND01681 described in Example 2, containing Gelucire® 44/14 and RyloMG18 9:1 w/w as components of the semi-solid matrix, are shown as a function of the manufacturing time. Samples of 0.5 ml were withdrawn from the molten mass stirred at 60° C., after 2 hours (column 'A') and 48 hours (column 'B') and partitioned in capsules. The dissolution rate tests were performed with the USP Basket method; 100 rpm; 37° C. in Simulated Gastric Fluid pH 1.2 without enzymes. The data are expressed as percent of the active released from the formulation. The theoretical unit dosage strength is 50 mg CPT-11 per capsule.

The results obtained clearly show that the longer is the molten mass stirring time at 60° C. before partitioning into capsules the lower is the release profile when the capsule formulation are tested for dissolution rate.

This effect, highlighted during a control in process of the manufacturing process, can be considered predictive of what is going to happen to formulations with aging.

TABLE 4

| Time | Percent of CPT-11 released from the formulation | |
|---|---|---|
| (minutes) | 'A' | 'B' |
| 15 | 9.74 | 3.32 |
| 30 | 28.31 | 13.73 |
| 60 | 61.12 | 36.85 |
| 120 | 87.18 | 67.53 |
| 180 | 87.47 | 81.63 |
| 240 | 87.45 | 83.63 |

Example 5

In the following Table 5 the dissolution rate profiles of CPT-11 from the formulation ND01672 described in Example 2, containing Gelucire® 44/14 and Epikuron135F 9:1 v/v as components of the semi-solid matrix, are shown as a function of the manufacturing time. Samples of 0.5 ml were withdrawn from the molten mass stirred at 60° C., after 2 hours (column 'A') and 48 hours (column 'B') and partitioned in capsules.

The dissolution rate tests were performed with the USP Basket method; 100 rpm; 37° C. in Simulated Gastric Fluid pH 1.2 without enzymes. The data are expressed as percent of the active released from the formulation. The theoretical unit dosage strength is 50 mg CPT-11 per capsule.

The results obtained clearly show that the drug dissolution rate is not influenced by the stirring time of the molten mass before partitioning into capsules. In fact, the dissolution release profiles obtained from capsules manufactured both after 2 and 48 hours of stirring at 60° C. are superimposable.

This effect, highlighted during a control in process of the manufacturing process, can be considered predictive of what is going to happen to formulations with aging.

TABLE 5

| Time | Percent of CPT-11 released from the formulation | |
|---|---|---|
| (minutes) | 'A' | 'B' |
| 15 | 16.01 | 31.86 |
| 30 | 54.28 | 64.71 |
| 60 | 88.07 | 87.72 |
| 120 | 91.73 | 89.10 |
| 180 | 91.98 | 89.16 |
| 240 | 92.45 | 89.59 |

Example 6

In the following example the stability results of a formulation containing 50 mg/capsule of CPT-11 dispersed in a mixture of Gelucire® 44/14 are shown.

Method of Preparation

Preparation of CPT-11 Bulk Dispersion

1) In a suitable vessel or vial, melt about 50 mL of Gelucire® 44/14 at 60° C. under magnetic stirring.

2) Withdraw 40 mL of molten Gelucire® with a manual pipette and add it into a thermostated vessel or vial containing the pre-weighed amount of CPT-11 (4 g).

3) Disperse the drug in the molten matrix maintaining under stirring at 60° C. for about 4 hours Capsule Filling 1) Withdraw 0.610 ml samples of the CPT-11 bulk dispersion by means of a manual pipette and fill the capsules. Maintain the bulk dispersion at 60° C. and under constant stirring during the filling process.

2) Allow the filled capsules to cool at room temperature.

3) Package the manufactured capsules using a suitable conventional container

The capsules prepared as described above have been submitted to an accelerated stability plan and the results obtained are shown in Table 6.

TABLE 6

| Storage Conditions | Age (Months) | Assay (mg/cps) | Total related substances (% w/w) | Dissolution (% released in 60 minutes) |
|---|---|---|---|---|
| Initial | | 52.85 | 0.58 | 101 |
| 35° C. | 1 | 53.72 | 0.68 | 54 |

TABLE 6-continued

| Storage Conditions | Age (Months) | Assay (mg/cps) | Total related substances (% w/w) | Dissolution (% released in 60 minutes) |
|---|---|---|---|---|
| | 3 | 52.14 | 0.87 | 42 |
| | 6 | 51.27 | 0.86 | 36 |
| 40° C. 75% R.H. | 1 | 52.55 | 0.79 | 37 |
| | 3 | 50.07 | 0.84 | 61 |
| | 6 | 50.22 | 0.88 | 20 |
| Limits | | 45 to 55 | 1.50 | |

Legenda:
R.H.: relative humidity
mg/cps: milligrams per capsule
w/w: weight/weigth As clearly depicted in Table 6 an evident decrease in the drug dissolution rate from the dosage form has been experience with the CPT-11 semi-solid matrix formulation containing Gelucire® 44/14 as a carrier.

Example 7

In the following example the stability results of a formulation containing 50 mg/capsule of CPT-11 dispersed in a mixture of Gelucire® 44/14 and Epikuron135F are shown.

Method of Preparation

Preparation of CPT-11 Bulk Dispersion

1) In a suitable vessel or vial, melt about 80 mL of Gelucire® 44/14 at 60° C. under magnetic stirring.

2) Withdraw 72 mL of molten Gelucire® with a manual pipette and add it into a thermostated vessel or vial 3) Add 8 mL, exactly measured with a manual suitable pipette, of Epikuron135F to the molten Gelucire®

4) Stir gently at 60° C. till an homogeneous mixture is obtained

5) Add 70 mL of the Gelucire®/Epikuron molten matrix to a suitable thermostated vessel or vial containing the pre-weighed amount of CPT-11 (7 g).

6) Disperse the drug in the molten matrix maintaining under stirring at 60° C. for about 4 hours Capsule Filling 1) Withdraw 0.610 ml samples of the CPT-11 bulk dispersion by means of a manual pipette and fill the capsules. Maintain the bulk dispersion at 60° C. and under constant stirring during the filling process.

2) Allow the filled capsules to cool at room temperature.

3) Package the manufactured capsules using a suitable conventional container

The capsules prepared as described above have been submitted to an accelerated stability plan and the results obtained are shown in Table 7.

TABLE 7

| Storage Conditions | Age (Months) | Assay (mg/cps) | Total related substances (% w/w) | Dissolution (% released in 60 minutes) |
|---|---|---|---|---|
| Initial | | 53.42 | 0.50 | 97 |
| 35° C. | 1 | 52.61 | 0.59 | 97 |
| | 3 | 51.23 | 0.60 | 104 |
| | 6 | 50.92 | 0.58 | 100 |
| 40° C. | 1 | 53.42 | 0.55 | 92 |
| 75% RH | 3 | 51.57 | 0.69 | 107 |
| | 6 | 50.14 | 0.73 | 95 |
| Limits | | 45 to 55 | 1.50 | |

Legenda:
R.H.: relative humidity
mg/cps: milligrams per capsule
w/w: weight/weigth As clearly shown in the above Table 7, no changes both in dissolution profile and in chemical strength of the formulation is highlighted when CPT-11 is formulated into a gelucire/lecithin based formulation. This is in contrast with what has been shown in the previous example 6, where CPT-11 was formulated only into gelucire.

The invention claimed is:

1. A pharmaceutical composition suitable for oral administration which comprises irinotecan or a pharmaceutically acceptable salt thereof, a pharmaceutically acceptable carrier matrix which is a polyglycolized glyceride wherein the carrier matrix comprises from about 80% to about 95% (w/w) of the pharmaceutical composition, and from about 5% to about 15% (w/w) of lecithin, and wherein the polyglycolized glycerides has a melting point of about 44° C. and a hydrophobic-lipophilic balance of about 14.

2. The composition according to claim 1, wherein said Irinotecan or a pharmaceutically acceptable salt thereof irinotecan hydrochloride.

3. The composition as defined claim 1, which further comprises an agent selected from the group consisting of a dispersing agent, a solubilizing agent, a surfactant, a viscosity modifier, an oral absorption promoter, an antioxidant, and a chelating agent.

4. An oral formulation which comprises a capsule shell and, as a filling, the composition as defined in claim 1.

5. A process for producing the pharmaceutical composition as defined in claim 1, which process comprises adding lecithin to a hot molten dispersion of a pharmaceutically acceptable salt of irinotecan in the polyglycolized glyceride.

6. A process for producing the pharmaceutical composition as defined in claim 1, which process comprises dispersing or a pharmaceutically acceptable salt of irinotecan in a molten homogenous mixture of the polyglycolized glyceride and lecithin.

7. The composition as defined in claim 1, which further comprises one or more additional active drug substances selected from the group consisting of an antitumor antibiotic, a thymidylate synthase inhibitor, an epidermal growth factor receptor inhibitor, an antimicrotubule agent, an angiogenesis inhibitor, a chemosensitizer; a cyclooxygenase-2 (COX-2) inhibitor, an aromatase inhibitor; an alkylating agent, an antimetabolite, a hormonal agent, a platinum analog, octreotide, glutamine and leucovorin.

8. A method of preparing a medicament for oral administration in the treatment of a tumor, said method comprising mixing a hot molten dispersion comprising a pharmaceutically acceptable salt of irinotecan from about 80% to about 95% (w/w) of a polyglycolized glyceride, and from about 5% to about 15% (w/w) of lecithin.

9. The composition as claimed in claim 3, wherein the chemical stabilizing-promoting agent is an antioxidant or a chelating agent.

10. The composition of claim 7, wherein the antitumor antibiotic is an anthracycline.

11. The composition of claim 7, wherein the thymidylate synthase inhibitor is capecitabine.

12. The composition of claim 7, wherein the antimicrotubule agent is a taxane.

13. The composition of claim 12, wherein the taxane is a paclitaxel alkaloid, a docetaxel alkaloid or a vinea alkaloid.

14. The composition of claim 7, wherein the angiogenesis inhibitor is thalidomide, 3-(2,4-dimethylpyrrol-5-yl)methylidene-inodolin-2-one or (Z)-3-(2,4-dimethyl-5-(2-oxo-1,2-dihydro-indol-3-ylidenemethyl)-1H-pyrrol-3-yl)-propionic acid.

15. The composition of claim 7, wherein the cyclooxygenase-2 inhibitor is celecoxib, valdexocib, parecoxib or rofecoxib.

16. The composition of claim 7, wherein the alkylating agent is estramustine phosphate.

17. The composition of claim 7, wherein the hormonal agent is tamoxifen.

18. The composition of claim 7, wherein the platinum analog is cisplatin, carboplatin or oxaliplatin.

19. The composition according to claim 1, wherein the lecithin is a soy bean lecithin.

* * * * *